United States Patent [19]

Paletta et al.

[11] 4,345,483
[45] Aug. 24, 1982

[54] METERING APPARATUS

[75] Inventors: Benno Paletta; Reinhard Möller, both of Graz, Austria; Joachim Kasielke, Brühl, Fed. Rep. of Germany

[73] Assignee: Clinicon International GmbH, Mannheim, Fed. Rep. of Germany

[21] Appl. No.: 183,794

[22] Filed: Sep. 4, 1980

[30] Foreign Application Priority Data

Sep. 13, 1979 [DE] Fed. Rep. of Germany ....... 2937066

[51] Int. Cl.³ ............................................... B01L 3/02
[52] U.S. Cl. ................................... 73/864.16; 422/100
[58] Field of Search ..................... 73/864.16; 422/100; 128/DIG. 1; 222/41, 47, 63, 309

[56] References Cited

U.S. PATENT DOCUMENTS

| | | |
|---|---|---|
| 3,756,456 | 9/1973 | Georgi . |
| 3,796,239 | 3/1974 | Zindler et al. |
| 3,858,581 | 1/1975 | Kamen .......................... 128/DIG. 1 |
| 3,915,651 | 10/1975 | Nishi ................................ 73/864.16 |
| 4,101,283 | 7/1978 | Sundstrom ....................... 73/864.16 |
| 4,137,913 | 2/1979 | Georgi ................................... 222/63 |
| 4,223,558 | 9/1980 | Schmider ............................ 422/100 |

Primary Examiner—S. Clement Swisher
Attorney, Agent, or Firm—Sprung, Horn, Kramer & Woods

[57] ABSTRACT

The metering apparatus for small volumes of liquid in the milliliter and microliter range comprises a piston/cylinder system driven by a direct-current motor. The piston stroke is measured by means of an optical path-length measuring system. For this purpose, a slide-rule pulse scale provided with a regular line grid is affixed to the piston. The light from a light transmitter passes through the slide-rule pulse scale and a stationary scanning plate which likewise is provided with a regular line grid, and to a light receiver. The pulses of the light receiver are digitalized in a pulse conditioning circuit and fed to a counter adapted to be preset by means of a coding switch. The counter position acts upon a braking and rotative-speed regulating circuit in such a way that regardless of the preset desired value of the rotative speed the speed of rotation of the motor is reduced to a small value as the final value is approached. As soon as the preset volume has been metered and the counter has reached the zero position, the motor is brought to a dead stop through a motor-control logic circuit with the aid of a reverse voltage. During the stopping process the no-load voltage of the motor is measured by means of a zero-voltage comparator at regular intervals. A pulse monitoring circuit serves to measure and regulate the piston-stroke speed and to turn off the motor in case of a mechanical defect. Motor and electronic systems are supplied with current from dry cells or storage batteries, a power supply being optionally provided to charge them.

22 Claims, 12 Drawing Figures

METERING APPARATUS

BACKGROUND OF THE INVENTION

The invention relates to a metering apparatus for liquids, particularly for use in clinical chemistry, comprising a motor-driven piston/cylinder system; an optical position-determining system whose transparent pulse scale, provided with nontransparent marks, is affixed to the piston; an optical/digital measuring circuit which converts the stroke of the piston into a corresponding number of digital pulses; and a control, computer and comparator circuit which incorporates a counter counting the digital pulses and which controls the stroke of the piston on the basis of the preselected volume to be metered.

An apparatus of this type is known from U.S. Pat. No. 3,796,239. That reference discloses a desk set which must be connected to the electric line. The piston/cylinder system is driven by an AC-powered reversible motor having two windings, one for the forward and one for the reverse direction. Attached to the piston is a transparent slide-rule scale having four marks which correspond to the volumes of 25, 50, 100 and 200 microliters. These marks are optically scanned. For this purpose, the transparent slide-rule scale moves between a light transmitter and a light receiver in the form of a differential photodiode. The information identifying the one of the four possible volumes that is to be dispensed is entered into the desk set as a program by means of a punched card. As soon as the programmed mark is recognized by the photocells, the current supply to the motor is shut off, and the friction of the transmission and of the piston is relied on to brake the momentum of the motor.

A further metering apparatus is known from U.S. Pat. No. 3,756,456. In that apparatus, the motion of the piston is transmitted to a disk which is provided with a regular line grid. Light is projected onto that disk through a scanning plate which is likewise provided with a regular line grid. Now while an optical position-determining system of this type is more accurate in principle than the one to which U.S. Pat. No. 3,796,239 relates, its accuracy is reduced by the slight slip which occurs between the disk and the piston.

As is explained in detail in U.S. Pat. No. 3,756,450, accuracy problems also arise from the fact that liquid to be metered keeps flowing even after the drive motor has been turned off. Allowance is made for this afterflow of liquid in that the counter in which the pulses coming from the rotating coding disk are registered in preset for a given number of pulses before the start of the metering operation. Since it is very difficult to determine the number to be so preset, the use of this expedient in everyday routine laboratory practice is out of the question. Besides, it increases the complexity of the required electronic circuitry since a counter and a counter-position comparator are additionally needed.

In any laboratory where serial analyses are performed, the various sequences of operations, and particularly the many metering operations, must be continually rendered more efficient. Now fully automatic analyzers call for high capital outlays, full utilization of their capacity, and specially trained personnel. Such equipment is of great complexity, and any malfunction entails expensive down time. This is why electronic metering apparatuses have been developed wherein the pistons of the metering syringes are moved either by means of electronically controlled stepping motors or, as described above, through alternating-current motors controlled by optical measuring systems. However, the size and weight of the motors and of the mechanical power-transmission system are such that these apparatuses must be constructed as stationary installations. This militates against ease of operation; and, in addition, such apparatus requires a continuous line-power supply. The size and weight of the apparatus are also reflected in its overall cost.

SUMMARY OF THE INVENTION

The present invention thus has as its object to provide a metering apparatus of the type outlined above which dispenses with heavy and costly high-precision mechanical parts, allows the metering of volumes of liquid with extremely high precision, permits all metering operations such as dispensing, diluting, pipeting, titrating, etc., to be performed, and has such low current consumption that it can be operated on built-in storage batteries or dry cells. It is intended for use with both portable and stationary apparatus.

This object is accomplished in that there is disposed, adjacent to the first pulse scale, a further pulse scale as a scanning plate in a position that is fixed relative to the cylinder; that a light transmitter and a light receiver are provided for the transmissive or reflective scanning of the pulses; that the marks on the pulse scales form a regular line grid; that the motor is a direct-current motor; that the speed of rotation of the motor is controlled on the basis of the counter position in such a way that when the preselected metered volume is approached the speed is set at minimum level; and that circuitry is provided to permit the motor to be brought to a dead stop by applying a reverse voltage to it when the counter position corresponding to the preselected metered volume is reached.

This offers the advantage that the volume measurement can be carried out with exceptional accuracy; that the transmission whereby the rotary motion of the motor is converted to the motion of the piston can be constructed in a very simple manner and at low cost; and that the piston stroke can be measured directly, optically, with high precision. A further considerable advantage is that the use of a DC motor, and preferably of a small bell-type armature motor, makes possible a very compact and light-weight construction of the piston-stroke pipette and its mechanical drive, thus readily permitting them to be hand-held even though they possess or even exceed the advantageous properties of conventional, considerably larger apparatuses, such as high positioning accuracy and great holding power. This is due especially to the fact that the electronic control circuit in accordance with the invention permits the rotary motion of the motor to be stopped abruptly so that the high measuring accuracy provided by the optical measuring system employed can be translated into a correspondingly high metering accuracy.

The optical measuring system used to measure the piston stroke is termed a digital incremental measuring system and in principle is known, for example, from the German technical journal BBC-NACHRICHTEN, September 1967, pages 464 to 471, and particularly page 468. While such systems have already proved themselves in many technical sectors and permit resolution down to one micron, they are not known to have been employed up to now in the form of a slide-rule scale in metering apparatus of the type here involved.

It is preferable that the light transmitter in the optical position-determining system be a light-emitting diode, the light receiver be a photodiode, the light receiver be followed by a voltage comparator, and a differentiator be inserted between light receiver and voltage comparator. These components together form an analog-to-digital converter which converts the optical analog signal received by the light received into a digital signal suited for further processing in the digital control, computer and comparator circuit.

In accordance with an advantageous embodiment of the invention, the control, computer and comparator circuit incorporates a rotative-speed control circuit whereby the motor is accelerated to the preselected speed level and before the preselected volume is reached is decelerated to the lowest speed level by a given number of optical pulse steps. In this way, a high metering speed coupled with high metering accuracy is achieved. If the motor were not decelerated to the lowest speed level before the preset volume was reached, the requisite high metering accuracy could not be obtained even with the braking circuit in accordance with the invention, to be described further on.

The rotative-speed regulating circuit preferably includes a regulated voltage source whose output voltage is the motor operating voltage and whose desired value is variable in several steps. Moreover, with a small volume to be handled, the rotative-speed regulating circuit is at all times set for the lowest speed level. As the drive motor is being stopped, a reverse voltage is momentarily applied to it; however, the maximum permissible motor operating voltage is not exceeded in order that the service life of the motor may not be shortened.

As the motor is being stopped and a reverse voltage is being applied to it, said reverse voltage is, in accordance with a preferred embodiment of the invention, periodically shut off. While the motor runs freely, the no-load voltage is measured, the disappearance of the no-load voltage indicating that the motor has stopped. These measurements are effected continuously and at short intervals of time so that overbraking of the motor is avoided or at least minimized to such an extent that the pipeting accuracy is not adversely affected thereby.

It should be noted that the transmission in the pipette control in accordance with the invention need not be fabricated to high precision and may have some play.

For the measurement of the no-load motor voltage, a zero-voltage comparator is provided which upon the disappearance of the no-load voltage delivers an output signal. The measuring input of the zero-voltage comparator is preferably connected to the motor terminals through a voltage divider. The zero-voltage comparator is preferably an appropriately wired operational amplifier. Connecting the comparator through a voltage divider has the advantage that but one comparator need to be used for the two directions of rotation of the motor since the center-tap voltage of the voltage divider always has the same polarity relative to the reference electrode of the circuit. The fact that because of the use of a voltage divider the voltage applied to the measuring input of the comparator is halved can readily be compensated by appropriately increasing the amplification of the comparator.

The motor is preferably arranged in a bridge circuit of four transistors. By turning on two diagonally opposed transistors, the motor camn be switched from forward to reverse without the polarity of the motor operating voltage applied to the bridge circuit having to be reversed.

The transistor bridge circuit is advantageously preceded by a function selector switch for changeover of the motor from forward to reverse or vice versa. The function selector switch is preceded by a motor-control logic circuit whereby in the motor operating phase two diagonally opposed transistors are turned on, in the motor stopping phase one of the two transistors is periodically turned off momentarily, and upon the stopping of the motor the transistors are turned on so that the motor is short-circuited. The motor-control logic circuit forms from the signals specified by the control circuit, such as RUN MOTOR, STOP MOTOR, or MEASURE MOTOR ROTATIVE SPEED, the trigger pulses for the transistors of the bridge circuit. Depending on whether the motor is to turn in the forward or reverse direction, the function selector switch, in turn, distributes these trigger pulses to the transistors enabling the desired motor function.

In accordance with an advantageous embodiment of the invention, a resistor is disposed in the current feed to the transistor bridge circuit, and the voltage drop at that resistor serves as actual value for the rotative-speed regulating circuit. The voltage drop at that resistor, which is directly proportionate to the current through the motor, may further be used to limit the motor current to the maximum permissible value.

In accordance with another advantageous embodiment of the invention, a clock generator delivering markedly asymmetrical pulses is provided for periodically turning off momentarily one of the two transistors carrying the braking current, the long pulses defining the braking phase while the short pulses define the measuring phase. During the motor stopping phase one of the two transistors carrying the braking current is turned off for the duration of the short pulses whereas it remains turned on for the duration of the long pulses. This means that during the longer interval of time the motor is being actively braked, and that during a short interval it is isolated from the motor operating voltage and is in the no-load condition.

There is preferably provided a measured and stopping logic circuit which during the short pulses from the clock generator determines the time of measurement and during the motor stopping phase keeps transmitting pulses to the motor-control logic circuit until the zero-voltage signal from the zero-voltage comparator appears. This circuit makes it possible for the interrogation of the measured results to be initially delayed by a given short period during the stopping phase, after one of the two transistors carrying the braking current has been turned off, and when the measurement of the no-load voltage of the motor, which takes place during that period, is to be made, such delay being necessary as otherwise the evaluation might be based on the inductive voltage surge due to the turning off of the braking current in the motor rather than on the no-load voltage, which, of course, would produce a wholly erroneous result.

The circuit for the presetting and comparing of the volume to be handled advantageously comprises an externally presettable counter, an externally operable manual starting means for the counter, a counter input for the pulses from the position-determining system, and a system for the recognition of small volumes whose output is connected to the rotative-speed regulating circuit and sets the latter for the lowest speed level. Presetting of the volume to be handled may be done by means of a plurality of decade selector switches, for example. As soon as the start key is pressed to initiate a metering operation, the starting means first causes the numbers set at the decade selector switches to be transferred to the counter, then causing the motor to be started through the motor-control logic circuit, the function selector switch and the rotative-speed regulating circuit; causing, with small volumes which either have been selected in advance or are due to the fact that the piston has meanwhile approached its target value, the rotative-speed regulating circuit to be set for the lowest speed level; causing the pulses coming from the optical measuring system for the piston advance to be subtracted from the set counter position; and causing the measuring and stopping logic circuit to be energized when the counter position is zero.

In accordance with a further advantageous embodiment of the invention, there is provided a fully automatic piston starting-point seeking circuit which monitors the number of optical pulse steps produced in unit time and shuts off the current supply to the motor when no pulses are produced in unit time. Such a circuit permits the piston of a pipette inserted in the portable apparatus to be positively set to zero regardless of the actual length of the pipette or its piston. This circuit further makes it possible to advance the piston by means of the motor fully automatically as far as the cylinder stop. Moreover, in case of a malfunction of the normal piston advance, this circuit permits the motor to be switched off before it or the transmission is overloaded. In the absence of optical pulses, the piston starting-point seeking circuit produces a zero-setting pulse that resets the counter to zero and thus initiates the motor-stopping procedure.

In accordance with a preferred embodiment of the invention, the number of output pulses of the position-determining system in unit time is used as a measure of the rate of piston travel for regulation of the speed of rotation of the motor. This has the advantage that the rate of piston travel is measured with exceptional accuracy by the position-determining system, and it also facilitates digital signal processing.

In accordance with still another embodiment of the invention, an optical pulse integrator is provided which integrates the output pulses of the optical position-determining system and transmits them as actual value of the rate of piston travel to the regulated voltage source for the motor operating voltage. In this variant, the rate of piston travel is regulated directly and not by way of the motor current.

In accordance with a preferred embodiment, the regulated voltage source for the motor operating voltage is constructed as a clocked voltage source with variable pulse/pause ratio. A clocked voltage source has very high efficiency and a low output resistance. The high efficiency is of advantage particularly when the metering apparatus is operated on storage batteries or dry cells. The low output resistance aids the abrupt braking of the motor, especially during stopping, and thus contributes to the high metering accuracy. Moreover, a voltage source of this type is commercially available as an integrated circuit.

It is particularly advantageous for the transistors of the bridge circuit is also form part of the clocked voltage source, as the cost of the electronic circuit then is reduced to a minimum.

BRIEF DESCRIPTION OF THE DRAWINGS

The invention will now be explained in greater detail with reference to embodiments illustrated in the accompanying drawings, wherein.

DETAILED DESCRIPTION OF THE INVENTION

Figure 1:
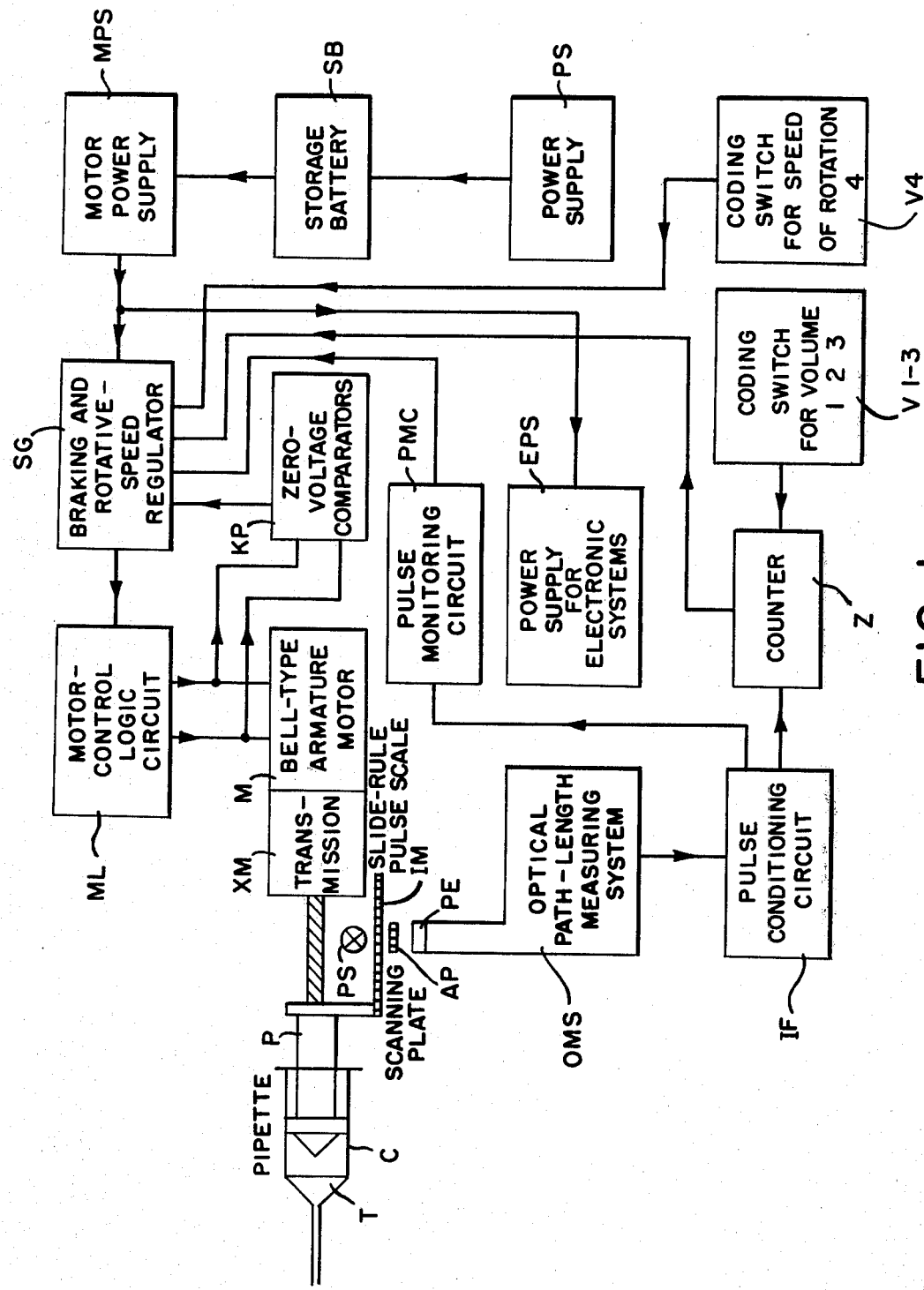
FIG. 1 is a block diagram of the electronic control, computer and comparator circuit of a metering apparatus.

Shown on the left in the block diagram of FIG. 1 is a pipette PP consisting of a cylinder C, a piston P adapted to move therein, and a preferably replaceable disposable tip T. The piston is driven by a small direct-current motor M through a transmission XM. Affixed to the piston is a slide-rule pulse scale through which light from a light source passes. On the side of the slide-rule pulse scale IM facing away from the light source PS there is disposed a light receiver PE which is part of an optical path-length measuring system OMS. Disposed between light receiver PE and slide-rule pulse scale IM is further a stationary scanning plate AP. The scanning plate AP and slide-rule pulse scale IM are transparent and provided with a regular, nontransparent line grid. The lines of these grids extend substantially perpendicularly to the direction of motion of the slide-rule pulse scale, some angular deviation being quite permissible. The accuracy of the line grid substantially determines the accuracy of the piston movement, and hence the metering accuracy.

In place of the transmissive scanning described, in which the measuring light passes through the two pulse scales, reflective scanning may be employed, with the light source and the light receiver then being located on the same side of the two pulse scales. In this case, the pulse scale facing away from the light source and the light receiver is preferably, but not necessarily, nontransparent.

In a pulse conditioning system, the electrical pulses produced by the optical path-length measuring system OMS are put into proper shape for digital processsing by pulse conditioning circuit IF and then fed to a counter Z. Counter Z is adapted to be preset by a volume coding switch V1–V3, and it will then count backward from the preset number until the number 0 is reached.

The instantaneous position of the counter Z controls a braking and rotative-speed regulating circuit SG. The rotative-speed regulating circuit may be set for different speed levels by means of a further coding switch. The rotative-speed regulating circuit acts upon a motor-control logic circuit ML which supplies the motor M with its operating voltage. The voltage at the motor terminals is measured through a zero-voltage comparator KP which during the motor stopping phase acts upon the braking-voltage regulating circuit in such a way that the motor is actively braked by means of reverse voltage; that the braking voltage is immediately turned off when the motor is at rest; and that the motor terminals are then short-circuited.

The electronic circuits and the motor are supplied with current through a power supply PS which during idle periods charges a storage battery SB which during operation provides the current for the motor power supply MPS and for the electronic circuits power supply EPS.

Between the pulse conditioning circuit IF and the braking and rotative-speed regulating circuit SG, there is further inserted a pulse-monitoring circuit PM. The latter causes the number of optical pulses in unit time, which is a measure for the rate of piston travel, to be reported to the rotative-speed regulating circuit SG, where it is compared with the value set for the speed of rotation by means of a coding switch V4.

Figure 2:
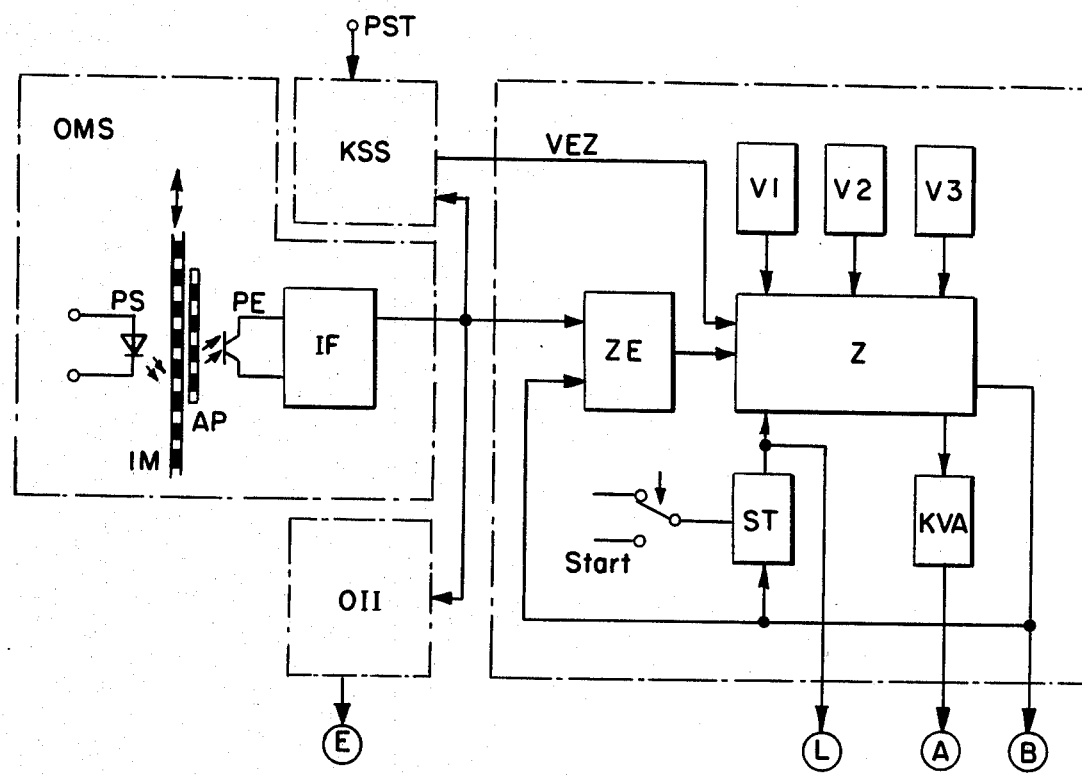
FIG. 2 is a block diagram of an optical path-measuring circuit including a pulse-shaping means.

Shown in the block diagram of FIG. 2 is the optical pathlength measuring system OMS comprising the light transmitter PS, the pulse scale IM, the scanning plate AP, the light receiver PE and the pulse shaper IF. Also shown is the presettable counter circuit VEZ comprising a counter Z, three coding switches V1, V2 and V3 a counter input circuit ZE, a starter circuit S and a recognition circuit KVA for small volumes. The presettable counter circuit VEZ furnishes three output signals, the output of the recognition circuit KVA for small volumes being applied to a terminal A, the zero output of the counter Z to a terminal B, and the output of the starter circuit ST to a terminal L. The pulses from the position-determining circuit OMS as well as the zero output of the counter Z are present at the input of the counter input circuit ZE. The latter will allow the pulses coming from the position-determining circuit OMS to pass until the counter Z has been decremented to 0 and the piston has traveled the preset distance.

There is further shown an automatic piston starting-point seeking circuit KSS to whose input the pulses from the position-determining circuit OMS are applied and whose output is connected to the zero-setting input of the counter. The command for initiation of the piston starting-point search is entered through a program start input PST.

Also shown is an optical pulse integrating circuit OII to whose input the output pulses of the automatic piston starting-point seeking circuit KSS are fed. The optical pulse integrating circuit OII delivers an output signal to the terminal E that is directly proportionate to the number of optical pulses arriving in unit time, and hence to the rate at which the slide-rule pulse scale IM affixed to the piston travels.

Figure 3:
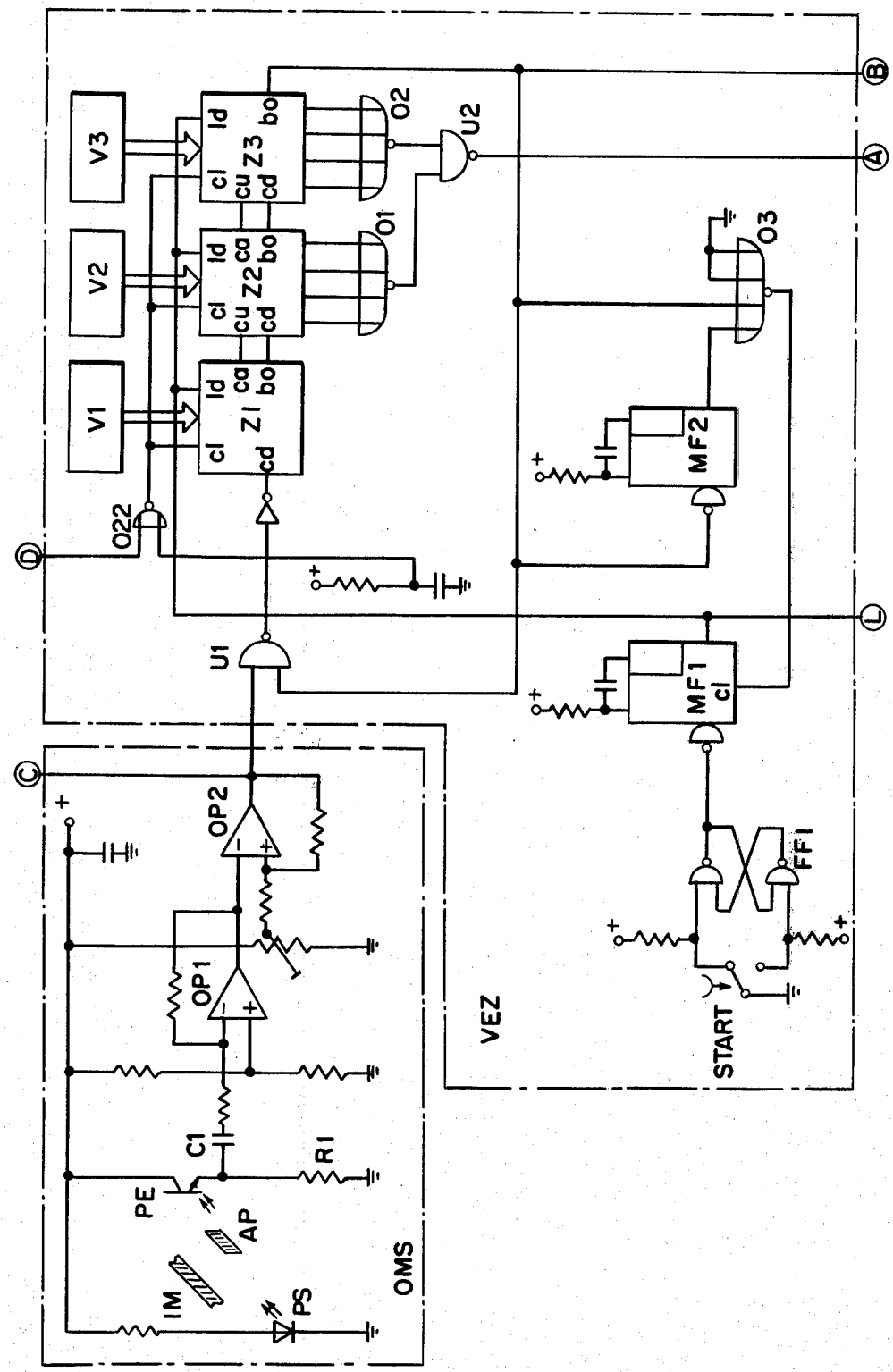
FIG. 3 illustrates one possible implementation of the circuitry of FIG. 2.

FIG. 3 illustrates an actual circuit which forms part of the position-determining circuit DMS and of the presettable counter VEZ shown in the block diagram of FIG. 2. Shown within the position-determining circuit OMS, bounded by a dash-dotted line, is the light transmitter PS in the form of a light-emitting diode the light from which passes through the slide-rule pulse scale IM and the scanning plate AP. The light is received by a phototransistor serving as light receiver PE and converted into an analog voltage. The output voltage of the phototransistor is fed through a differentiator R1 and C1 to a first operational amplifier OP2, wired as a voltage comparator. The pulses present at the output of the voltage comparator OP2 are routed to a terminal C, which is connected to the input of the automatic piston starting-point seeking circuit KSS, and to the presettable counter circuit VEZ. Connected to the input of the latter is a NAND gate U1 whose second input is connected to the output of the hundreds decade counter Z3. The pulses passing through the gate U1 are fed to the ones decade counter Z1 and from there pass to the tens decade counter Z2 and from the latter to the hundreds decade counter Z3. All three counters Z1, Z2 and Z3 are adapted to be preset by means of the decade selector switches V1, V2 and V3. The dual outputs of the tens decade counter Z2 and of the hundreds decade counter Z3 are each connected to a NOR gate 01 and 02, respectively. The two NOR gates 01 and 02 are linked through a NAND gate U2 and connected to the output terminal A.

The manual starting means consists of a starter key which is secured against chatter through a flip-flop FF1 following it. The start pulse of the flip-flop FF1 is converted through a monostable multivibrator MF1 with an inhibit input into a start pulse of defined duration. The inhibit input is to prevent the unintentional starting of a sequence of metering operations when the starter key is accidentally pressed repeatedly or when the starter key has a pronounced tendency to bounce. The start signal is routed to the three decade counters Z1, Z2 and Z3 and causes the numbers set at the switches V1, V2 and V3 to be transferred to the counters Z1, Z2 and Z3. At the same time, the start signal is applied to the terminal L. The inhibit signal for the monostable multivibrator MF1 is produced through a NOR gate 03 and a monostable multivibrator MF2 connected in parallel therewith. Also included in the circuit is a NOR gate 022, whose first input is preceded by an RC network whereby the counters Z1, Z2 and Z3 are positively set to zero when the operating voltage is switched on.

Through the second input of the gate 022, the output signal of the automatic piston starting-point seeking circuit KSS coming from the terminal D is applied to the clear inputs c1 of the counters Z1, Z2 and Z3. The makeup and principle of operation of the automatic piston starting-point seeking circuit KSS will be explained in conjunction with FIG. 8.

Figure 4:
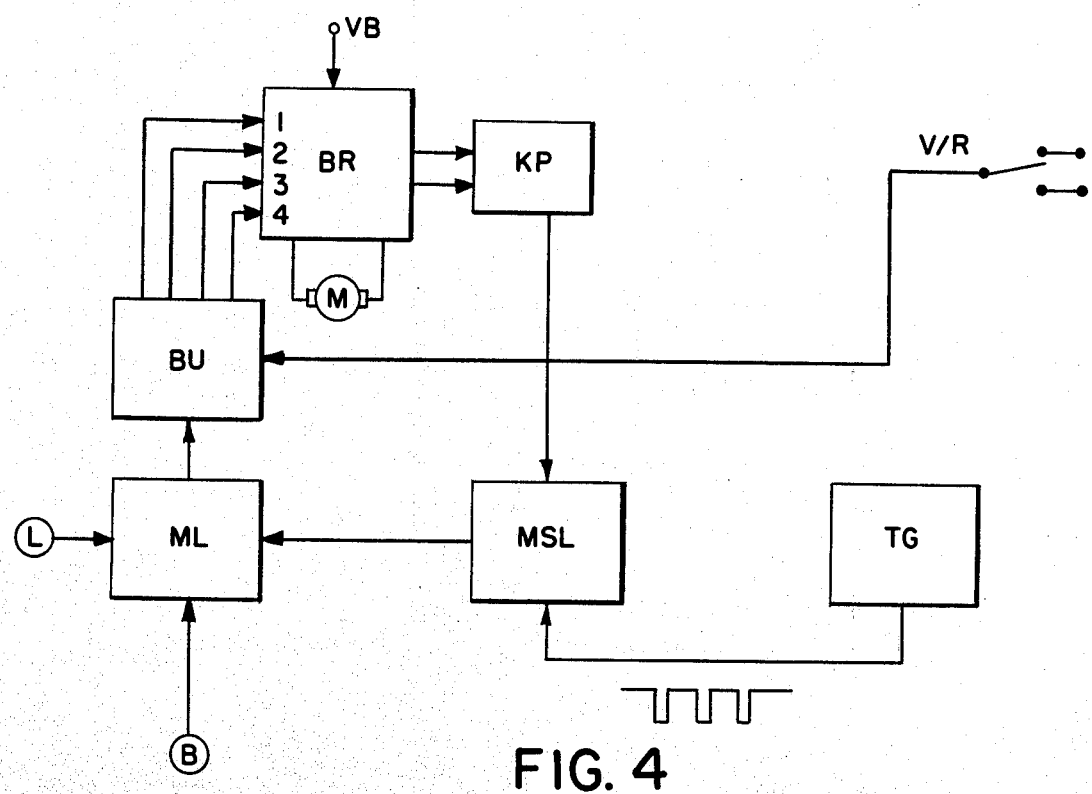
FIG. 4 is a block diagram of the portion of the control, computer and comparator circuit which relates to the forward and reverse operation of the motor and to its braking and stopping.

FIG. 4 shows the portion of the control, computer and comparator circuit relating to the motor functions RUN, BRAKE and STOP. The start pulse present at the terminal L is routed to a motor-control logic circuit ML whose output signal is converted through a function selector switch BU into four trigger signals for a bridge circuit BR. Connected to the latter is the direct-current motor M. In addition, a motor operating voltage VB is fed to the bridge circuit BR.

The braking signal present at the terminal B is further routed to the motor-control logic circuit ML. The function selector switch BU is under the control of the forward/reverse signal V/R. The V/R switch is set either by the operating personnel or automatically on the basis of the metering program set.

The motor no-load voltage is measured by a zero-voltage comparator KP. The output of the latter is connected to a measuring and stopping logic circuit MSL. At this logic circuit, the output signals of a clock generator TG are present. During the motor stopping phase, that is to say, when the braking signal is applied to terminal B, the clock generator TG will deliver output pulses to the motor-control logic circuit ML through the measuring and stopping logic circuit MSL until the signal indicating that the motor M is at rest arrives from the zero-voltage comparator KP. At that instant, the output pulses of the clock generator TG are inhibited and the motor-control logic circuit ML is activated in such a way that the motor M is short-circuited. The shorting of the stopped motor M provides the latter with increased resistance to mechanical movement due, for example, to forced displacement of the piston in the metering pipette.

Figure 5:
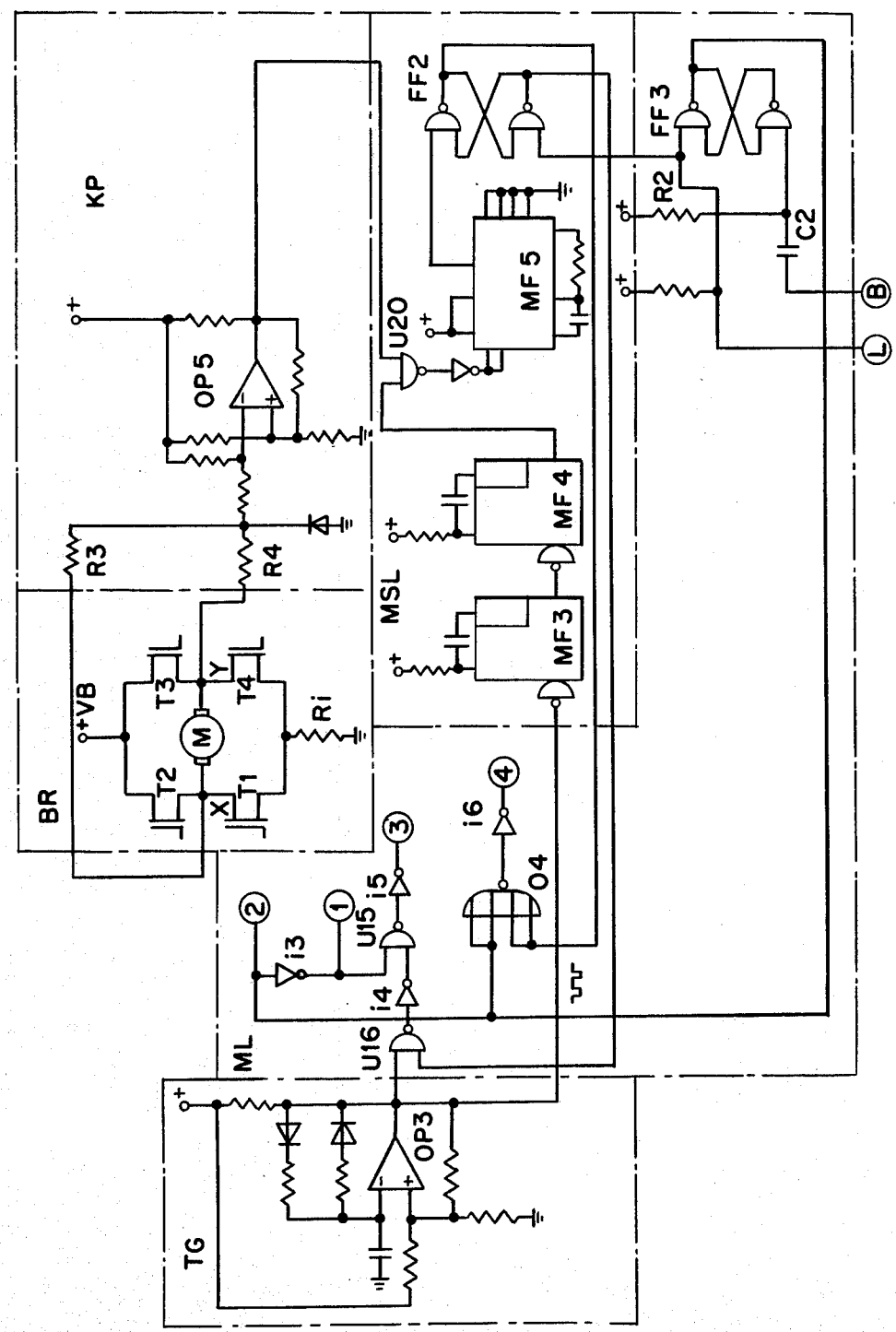
FIG. 5 illustrates a first possible implementation of the circuit portion of FIG. 4.

FIG. 5 illustrates a first circuit arrangement implementing the block diagram of FIG. 4. The clock generator TG consists of an operational amplifier OP3 wired as an astable multivibrator. The use of two diodes in a back-to-back configuration in the feedback path makes it possible to produce the desired markedly asymmetrical output-pulse signal.

The bridge circuit BR comprises four field-effect transistors T1, T2, T3 and T4 in one of whose diagonals the motor M is disposed. The motor operating voltage VB is fed to the other diagonal of the bridge, the connection between the transistor bridge and the reference electrode being established through a resistor $R_i$. A voltage proportionate to the motor current may be tapped off said resistor $R_i$. As will be described further on, that voltage can serve as actual value for the rotative-speed regulating circuit.

Figure 7:
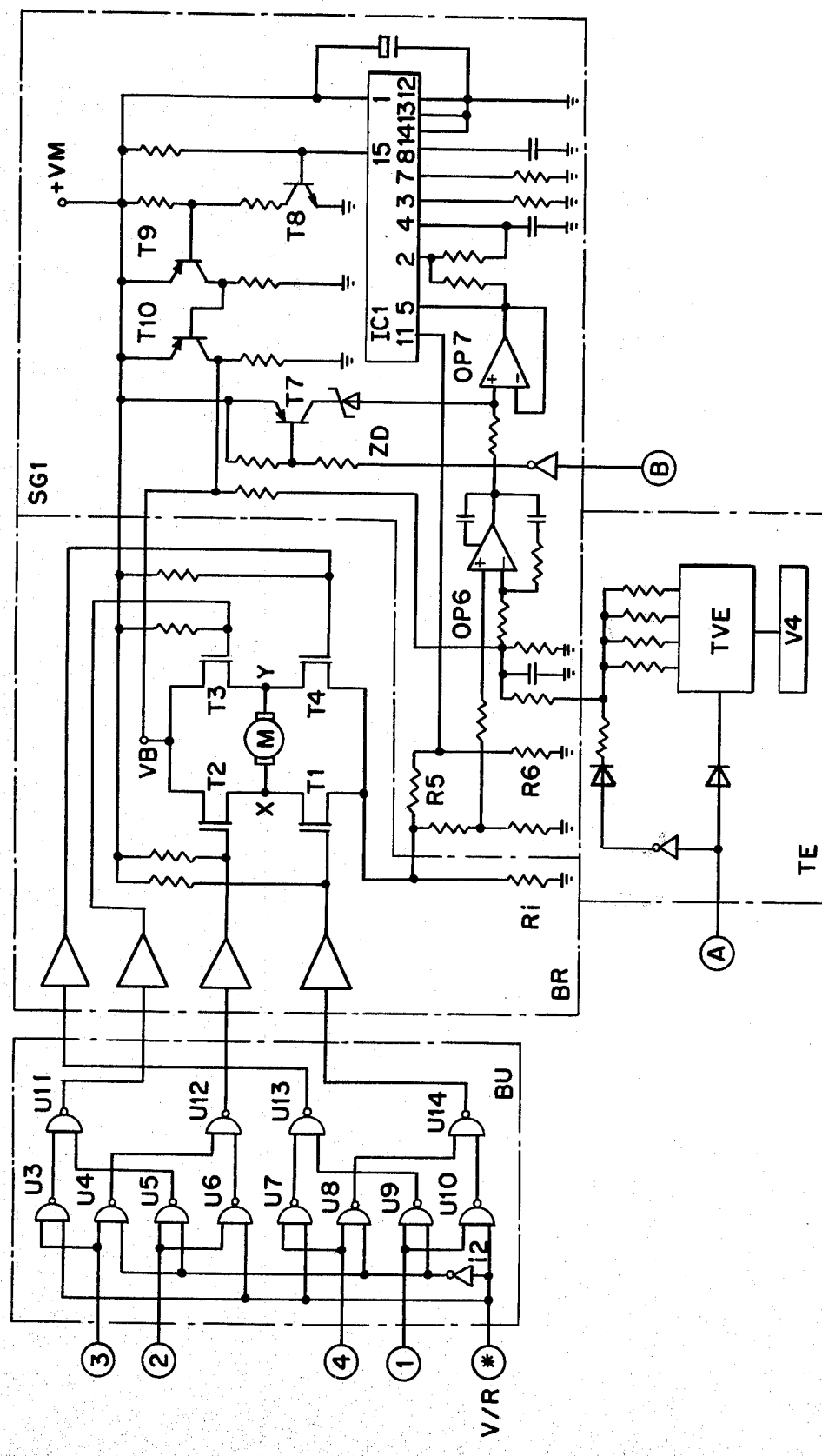
FIG. 7 illustrates a first possible implementation of a rotative-speed regulating circuit.

For greater clarity, the function selector switch BU which precedes the transistor bridge BR is not shown in FIG. 5; however, it is shown in FIG. 7.

The measuring input of a zero-voltage comparator KP is connected to the motor terminals through a voltage divider R3 and R4. Said zero-voltage comparator is a conventionally wired operational amplifier OP5. The output signal of the zero-voltage comparator KP is routed to a NAND gate U20. The second input of that gate, which is part of the measuring and stopping logic circuit MSL, is connected through two series-connected monostable multivibrators MF3 and MF4 to the output of the clock generator TG. The two monostable multivibrators MF3 and MF4 serve to delay and shape the output pulses of the clock generator TG. So long as the motor M is running, a signal will be present at the output of the comparator KP, and the output pulses of the monostable multivibrator MF4 will be routed through the NAND gate U20 to a retriggerable monostable multivibrator MF5. During that time, there is present at the output of the monostable multivibrator MF5 a continuous signal which triggers a succeeding flip-flop FF2 in such a way that the NAND gate U16 allows the output pulses of the clock generator TG to pass.

As the motor begins to run, the flip-flop FF2 is triggered by the start signal coming from the starter circuit and appearing at the terminal L to change state so that the NAND gate U16 will not allow the passage of the output pulses of the clock generator TG, which are needed only for the braking process. The upper output of flip-flop FF2 then pulses the motor-starting logic circuit ML in such a way that a continuous signal is applied to two diagonally disposed transistors T1 and T3 or T2 and T4, respectively, in the bridge circuit BR, depending on whether the motor M is to run in the forward or reverse direction.

At the start of the braking operation, that is to say, when the counter stands at zero, a braking signal is routed by way of the terminal B to the flip-flop FF3.

If initially the transistors T1 and T3 were conducting, then the transistors T2 and T4 are conducting now. A reverse voltage is thus applied to the motor. Moreover, the gate U16 now allows the pulses of the clock generator TG to pass.

During the short portions of the output pulses of the clock generator TG, the transistor T2 or T3, whichever is associated with the positive pole of the motor operating voltage VB, is momentarily turned off through the NAND gate U16 so that during that period the motor continues to run unbraked. The turned-on transistor T1 or T4 adjacent to the reference electrode continues to conduct to permit the no-load voltage of the motor to be measured by means of the zero-voltage comparator KP. The evaluation of this measurement must be delayed for a short period with respect to the turning off of transistor T2 or T3, respectively, to prevent the voltage surge due to the motor inductance from being measured. As pointed out earlier, this delay is produced by means of the two monostable multivibrators MF3 and MF4.

Figure 6:
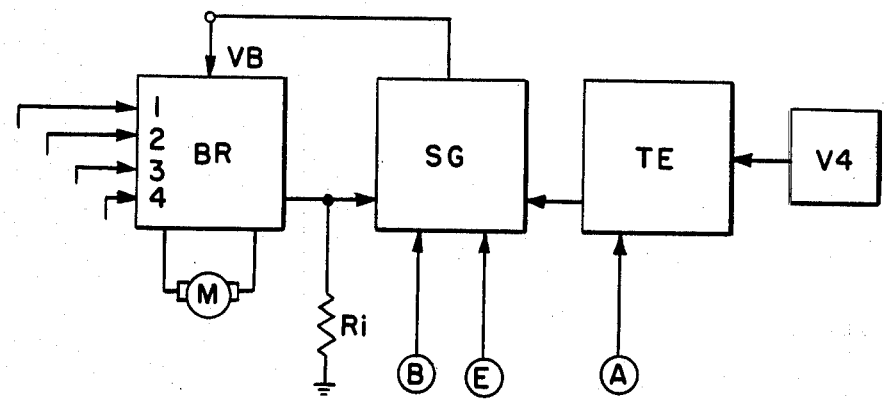
FIG. 6 is a block diagram of the rotative-speed regulating circuit.

FIG. 6 gives the block diagram for the rotative-speed regulating circuit. As is apparent, a fourth preselector V4 permitting several speed levels to be preset is provided. The position of the preselector switch V4 controls a speed-setting means TE. The output signal of the circuit KVA for the recognition of small volumes which appears at the terminal A is also routed to the speed-setting means TE, the latter being thus automatically reset to the lowest speed level in the presence of small volumes. The speed-setting means TE acts upon a voltage generator SG, which is implemented as a regulating circuit and compares the desired value furnished by the speed-setting means with the actual value of the drop at the resistor $R_i$ or furnished by way of the terminal E by the optical pulse integrating circuit OII. Through the braking signal present at terminal B, which, as pointed out earlier, appears when the counter has been decremented to zero, the voltage generator SG can be set for a braking-voltage value independently of the speed-setting means TE. The output quantity of the voltage generator SG is the motor operating voltage VB which is fed to the bridge circuit BR.

FIG. 7 illustrates a first implementation of a circuit corresponding to the block diagram of FIG. 6, there being further shown the function selector switch BU, which here is more readily recognizable. It consists of a network of twelve NAND gates, U3 to U14, and an inverter i2. By means of the forward/reverse signal present at the terminal V/R, either the gates U3, U6, U7 and U10 or the gates U4, U5, U8 and U9 can be made to pass the control signals coming from the motor-control logic circuit ML and appearing at the terminals 1, 2, 3 and 4. The gates U11, U12, U13 and U14 logically link these signals and route them by way of level converters to the control electrodes of the bridge transistors T1, T2, T3 and T4.

The voltage generator SG1 which serves as rotative-speed regulator comprises on the input side an operational amplifier OP6, wired as a PI (two-term) controller, whose positive input is connected through a voltage divider to the precision resistor $R_i$ of the transistor bridge BR and to the output of the speed-setting means TE. The output of the PI controller OP6 is routed through an isolation amplifier OP7 to an input 5 of the integrated circuit IC1, at whose output 15 a pulsed voltage having a pulse/pause ratio corresponding to the preselected speed level and the instantaneous motor load is present. The pulsed voltage at output 15 is amplified in an amplifier formed by the three transistors T8, T9 and T10 and delivered as motor operating voltage VB to the bridge circuit BR. A portion of the motor operating voltage VB is fed through a voltage divider, filtered by the use of a capacitor, and together with the output signal of the speed-setting means used as negative feedback at the negative input of the PI controller OP6. The internal resistance of a pulsed voltage source of this type is extremely low in relation to the motor resistance. Also the efficiency of such a pulsed voltage source is very high. The regulating circuit itself accelerates the motor when its speed is too low, and actively brakes it when it runs too fast. This will always be the case when a changeover is made from a high to a low speed level, for example.

The integrated circuit IC1 is a commercial control circuit for pulsed power supplies, such as circuit TDA 1060, sold by the German company Valvo. A portion of the voltage dropped at the precision resistor $R_i$ is applied to the input 11 of the integrated circuit IC1 through a voltage divider R5 and R6. Said voltage at input 11 serves to limit the maximum current. As soon as the voltage at the input 11 threatens to rise to too high a level, the pulse/pause ratio at the output 15 is changed so that the motor operating voltage VB drops sufficiently to assure that the current will not become too large.

The desired rotative-speed level can be set through the speed-setting means TE. The latter comprises a preselector V4 and a BCD switch which by means of the resistors disposed at its output acts upon the PI controller. By means of the signal for small volumes present at the input terminal A, the BCD switch may be bypassed so that the lowest speed level, that is to say, the lowest speed of rotation of the motor, is selected at all times.

As soon as the braking signal appears at the terminal B, a transistor T7 is turned on. Through the zener diode ZD located in its collector circuit, said transistor acts upon the voltage at the input 5 of the integrated circuit IC1 in such a way that regardless of the speed level selected it will deliver a constant motor operating voltage VB as braking voltage. The motor thus is actively braked with a high reverse voltage. The magnitude of the braking voltage is selected so that together with the voltage generated in the rotating motor winding the maximum permissible motor voltage is not exceeded in order that the service life of the motor not be shortened. In addition, the maximum-current limitation at the output 11 of IC1 remains effective.

Figure 8:
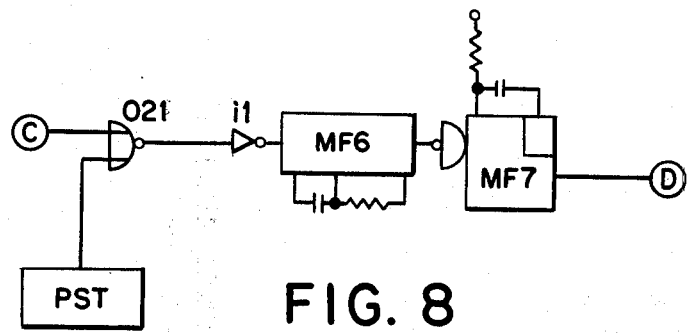
FIG. 8 illustrates a possible implementation of an automatic piston starting-point seeking circuit.

FIG. 8 illustrates an embodiment of the piston starting-point seeking circuit KSS. The output pulses of the position-determining circuit OMS are applied to the terminal C. Through the first input of the NOR gate 021 and an inverter i1 following it, they reach a retriggerable monostable multivibrator MF6. The time constant of the latter is selected so that signals will be present at the output for as long as pulses are produced by the position-determining system OMS. In the absence of pulses from the position-determining system OMS, the signal at the output of the retriggerable monostable multivibrator MF6 will disappear after a given length of time. This will actuate a monostable multivibrator MF7 to deliver to the terminal D a short signal. Said signal D is routed to the zero-setting inputs c1 of the counters Z1, Z2 and Z3, which are then set to zero. Now as soon as the counters stand at zero, the braking process is initiated, as described above, and the motor is stopped.

The purpose of the piston starting-point seeking circuit KSS is to fix the starting point of the piston stroke by causing the motor to force the piston against the end of the cylinder. This may prove necessary when a new pipette is inserted in the portable metering apparatus, for example, or during the changeover from one metering mode to another. To initiate the starting-point seeking procedure, a search-initiating signal PST is produced which starts the retriggerable monostable multivibrator MF6 and the motor M, not shown in the drawing, in the forward direction. As soon as the motor M begins to run, the slide-rule pulse scale IM coupled to the piston causes pulses to be generated in the position-determining circuit OMS which maintain the retriggerable monostable multivibrator MF6 in its unstable state until the piston abuts on the cylinder.

A further advantage of the piston starting-point seeking circuit KSS is that the motor is turned off even when the piston is prevented by a defect from moving freely. Overloading therefore cannot occur.

Figure 9:
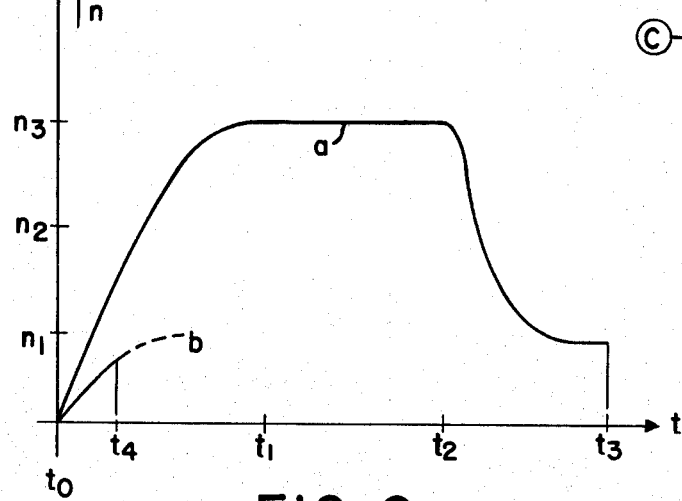
FIG. 9 is a plot of motor speed of rotation against various metered volumes to be handled and various metering speeds.

In FIG. 9, the speed of rotation n of the motor M is plotted against time t at various selected desired values of speed of rotation and metered volumes. As is apparent from curve a, the motor at time $t_0$ is accelerated from zero until it reaches its desired speed of rotation $n_3$ at time $t_1$. At this speed it continues to run until the recognition circuit for small volumes at time $t_2$ delivers an output signal to terminal A which causes the rotative-speed regulator to be set to the lowest speed level $n_1$. The speed of rotation n then drops to the value $n_1$. At time $t_3$ the preselected metering stroke is reached; the counter now stands at zero, and the motor is abruptly stopped. The speed of rotation then drops to 0.

Curve b illustrates the pattern of the speed of rotation when only a very small volume has been selected. From time $t_0$ on, the motor accelerates in accordance with the curve which is characteristic for the lowest speed level $n_1$. However, this final speed of rotation is not reached by the motor since the preselected volume is reached already at time $t_4$, the counter stands at zero, and the motor is abruptly braked down to speed 0.

Figure 10:
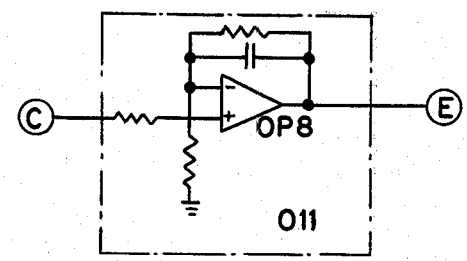
FIG. 10 illustrates an implementation of an optical pulse integrator.

FIG. 10 illustrates an embodiment of the optical pulse integrating circuit OII. The output pulses of the position-determining circuit OMS are applied to the terminal C of the operational amplifier OP8, wired as an integrator. The output voltage appearing at terminal E is directly proportionate to the number of pulses arriving in unit time at terminal C, which in turn corresponds to the rate at which the piston and the pulse scale affixed to it travel.

Figure 11:
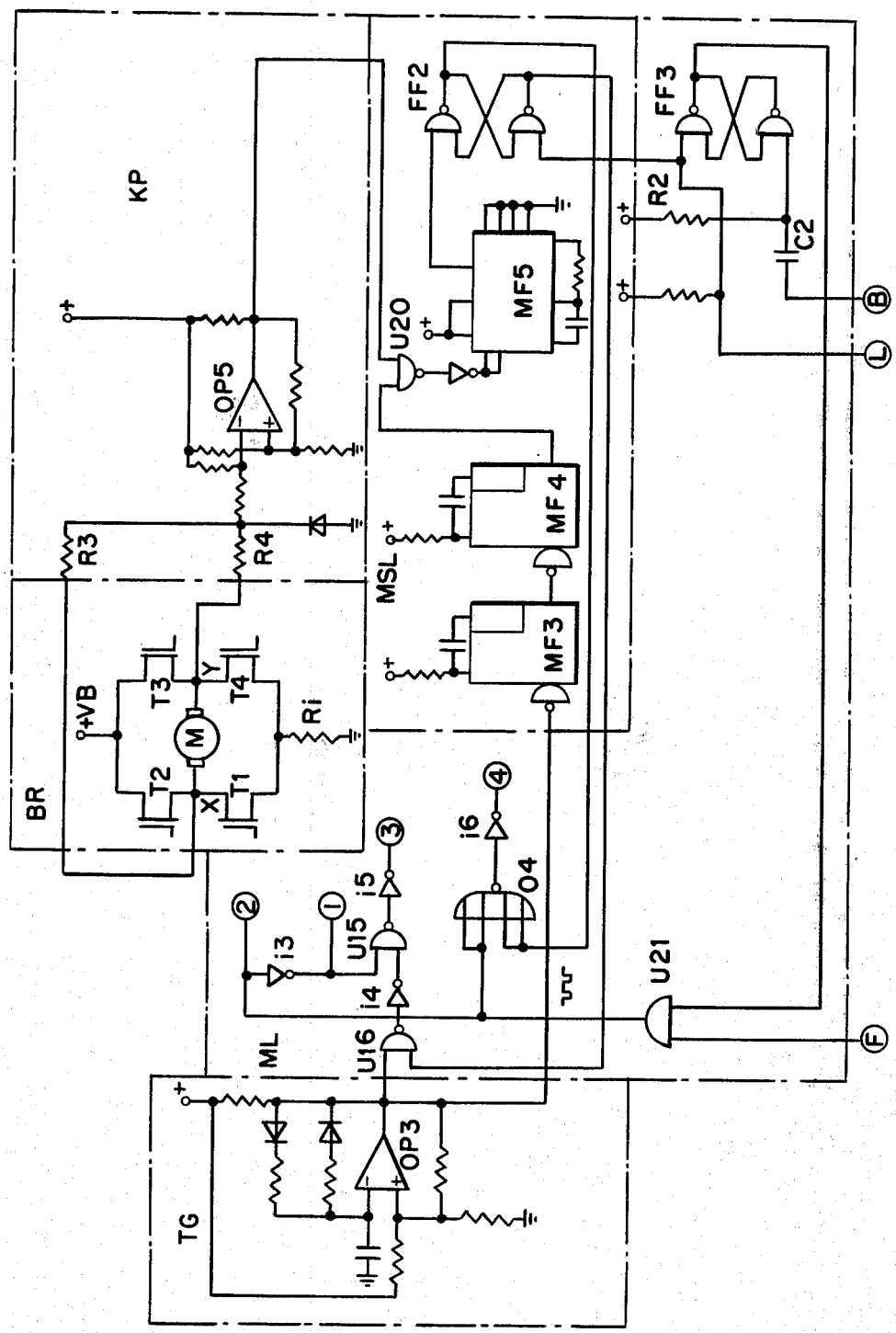
FIG. 11 illustrates a second possible implementation of the circuit of FIG. 4.

Shown in FIG. 11 is a second implementation of a circuit corresponding to the block diagram of FIG. 6, this implementation differing from that illustrated in FIG. 7 only in that an AND gate U21 is inserted in the line coming from the flip-flop FF3. The second input of the AND gate U21 is connected to a terminal F at which the pulsed voltage which comes from the input 15 of the integrated circuit IC1 and whose pulse/pause ratio corresponds to the preselected speed level and the instantaneous motor load is present. By means of the gate U21 it is thus possible to clock the transistors T1 and T3 or T2 and T4, respectively, of the bridge circuit BR in such a way that a voltage corresponding to the preselected speed level and the instantaneous motor load comes to be present at the motor M without a separate voltage amplifier, formed in FIG. 7 by the transistors T8, T9 and T10, being required. The transistors T1 to T4 of the bridge circuit and the gates and level converters which precede them simultaneously form part of the clocked voltage source.

Figure 12:
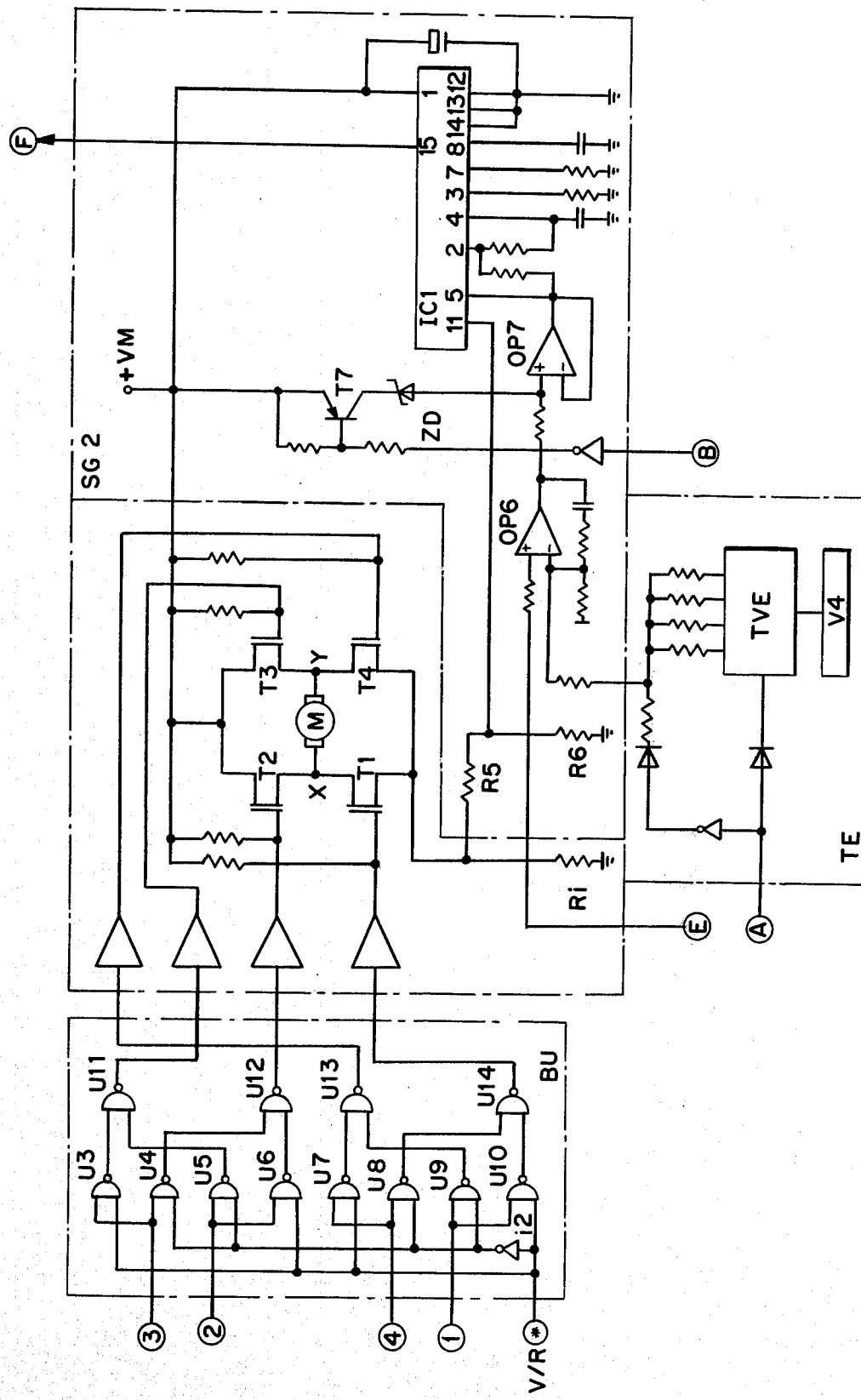
FIG. 12 illustrates a second possible implementation of of the rotative-speed regulating circuit.

The makeup of the modified voltage generator SG corresponding to FIG. 11 is illustrated in FIG. 12. Shown there is the operational amplifier OP6, wired as a PI controller, at whose positive input the output signal of the optical pulse integrating circuit OII which comes from terminal E and which is directly proportionate to the instantaneous rate of piston travel is present. The output signal of the speed-setting means TE is present at the negative input of the PI controller OP6 as the desired value. Through the operational amplifier OP7, wired as a buffer amplifier, the output voltage of the PI controller OP6 controls the integrated circuit IC1. The output 15 of the integrated circuit IC1 is routed to the terminal F, which is connected to the second input of the AND gate U21. A portion of the voltage drop across the precision resistor $R_i$ is again fed to the input 11 of the integrated circuit IC1 through the voltage divider R5 and R6 for limitation of the maximum current. In this embodiment, the upper end of the transistor bridge is directly connected to the unregulated motor supply voltage VM.

A numerical example will serve to illustrate the accuracy of the metering process obtainable with the metering apparatus in accordance with the invention. One such metering apparatus which has proved itself in practice has a stroke length of 60 mm, it being possible to meter with it volumes ranging from 0.005 to 12.5 ml, depending on the dimensions of the pipette tip. The stopping accuracy of the apparatus is better than 0.02 mm. This represents 0.033% of the stroke length. This accuracy is so high that the accuracy of the metering of volumes in practice depends solely on the precision of the tips used. The total duration of a pipetting operation is about 3 to 5 seconds.

It will be appreciated that the instant specification and claims are set forth by way of illustration and not of limitation, and that various changes and modifications may be made without departing from the spirit and scope of the present invention.

What is claimed is:

1. In a metering apparatus for liquids, having a motor-driven piston/cylinder system, optical position-determining means including a transparent pulse scale with nontransparent marks and affixed to the piston, an optical/digital measuring circuit which converts the stroke of the piston into a corresponding number of digital pulses, means including a counter for counting the digital pulses for controlling the stroke of the piston on the basis of a preset metering volume, the improvement wherein: the optical position-determining means further comprises a second pulse scale adjacent to the first pulse scale and fixed relative to the cylinder to form a scanning plate, and a light transmitter and a light receiver for the scanning of the marks, and the marks on the pulse scales form a regular line grid; the motor comprises a direct-current motor; and the means for controlling the stroke of the piston comprises means for controlling the speed of rotation of the motor on the basis of the contents of the counter such that when the preselected metering volume is approached the lowest speed level is selected, and braking means for applying a reverse voltage to the motor when the counter position corresponding to the preselected metering volume is reached to permit the motor to be brought to a dead stop.

2. The apparatus according to claim 1, wherein the light receiver is a phototransistor and the light transmitter a light-emitting diode, and wherein the optical position-determining means further comprises a voltage comparator following the light receiver and a differentiator between the light receiver and voltage comparator.

3. The apparatus according to claim 1 or claim 2, wherein the means for controlling the speed of rotation comprises a rotative-speed regulator which accelerates the motor to a preselected speed level and decelerates it in a given number of optical pulse steps to the lowest speed level before the preselected volume is reached.

4. The apparatus according to claim 3 wherein the rotative-speed regulator comprises a regulated voltage source whose output voltage is the motor operating voltage and having means for varying the output in several steps.

5. The apparatus according to claim 4, wherein the braking means brakes the motor from the lowest speed level to a stop without exceeding the maximum permissible values of the motor voltage.

6. The apparatus according to claim 5, wherein the braking means includes means for measuring the no-load voltage of the motor and means for periodically turning off the reverse voltage while the no-load voltage of the motor is being measured.

7. The apparatus according to claim 6, wherein the means for measuring the no-load voltage of the motor comprises a zero-voltage comparator which produces an output signal upon the disappearance of the no-load voltage.

8. The apparatus according to claim 7, wherein the measuring input of the zero-voltage comparator is connected to the motor terminals through a voltage divider.

9. The apparatus according to claim 8, wherein the zero-voltage comparator comprises an operational amplifier.

10. The apparatus according to claim 9, wherein the piston stroke control means comprises the motor disposed in a bridge circuit comprising four transistors.

11. The apparatus according to claim 10, wherein the bridge circuit further comprises a resistor disposed in the current feed to the transistor bridge circuit, and wherein the voltage drop across said resistor corresponds to the actual value for the rotative-speed regulator.

12. The apparatus according to claim 11, wherein the piston stroke control means further comprises a function selector switch preceding the bridge circuit for changeover of the motor to forward or reverse.

13. The apparatus according to claim 12, wherein the piston stroke control means further comprises a motor control logic circuit preceding the function selector for turning on two diagonally disposed transistors during the motor operating phase, turning off momentarily one of the two transistors during the motor stopping phase, periodically shortcircuiting the motor when it is at rest.

14. The apparatus according to claim 13, wherein the motor control logic circuit comprises, for the periodic momentary turning off of one of the two transistors carrying the braking current, a clock generator which produces markedly asymmetrical pulses, wherein the long pulses define the braking phase and the short pulses define the measuring phase.

15. The apparatus according to claim 14, wherein during the short pulses in the motor stopping phase one of the two transistors carrying the braking current is turned off and during the long pulses is turned on.

16. The apparatus according to claim 15, wherein the piston stroke control circuit further comprises a measuring and stopping logic circuit which during the short pulses of the clock generator fixes the time of measurement and during the motor braking phase keeps transmitting pulses to the motor control logic circuit until the zero-voltage signal of the zero-voltage comparator appears.

17. The apparatus according to claim 3, wherein the piston stroke control means further comprises means for presetting and comparing the volume to be handled including the counter which is an externally presettable backward counter, an externally operable manual starting means for the backward counter, a counter input circuit for the pulses from the position-determining system and a circuit for the recognition of small volumes having an output connected to the rotative-speed regulator for setting the latter to the lowest speed level.

18. The apparatus according to claim 1, further comprising a piston starting-point seeking circuit to monitor the number of optical pulse steps produced in unit time and for switching off the motor when no pulses are produced in unit time.

19. The apparatus according to claim 3, wherein the piston stroke control means includes means responsive to the number of output pulses of the position-determining system in unit time for measuring the rate of piston travel for regulation of the rotative speed of the motor.

20. The apparatus according to claim 19, wherein the means for measuring the rate of piston travel comprises an optical pulse integrator which integrates the output pulses of the position-determining means to produce a voltage proportionate to the rate of piston travel and a regulated voltage source for the motor operating voltage receptive of the voltage.

21. The apparatus according to claim 4, wherein the regulated voltage source for the motor operating voltage comprises a clocked voltage source with variable pulse/pause ratio.

22. The apparatus according to claim 21, wherein the transistors of the bridge circuit form part of the clocked voltage source.

* * * * *

UNITED STATES PATENT AND TRADEMARK OFFICE
CERTIFICATE OF CORRECTION

PATENT NO. : 4,345,483

DATED : August 24, 1982

INVENTOR(S) : Benno Paletta, et al

It is certified that error appears in the above—identified patent and that said Letters Patent is hereby corrected as shown below:

Col. 3, line 68        Delete "camn" and insert --can--

Col. 7, line 68        Delete "DMS" and insert --OMS--

Signed and Sealed this

Fourth Day of January 1983

[SEAL]

Attest:

Attesting Officer

GERALD J. MOSSINGHOFF

Commissioner of Patents and Trademarks